US009384548B1

(12) United States Patent
Wahrenberg

(10) Patent No.: US 9,384,548 B1
(45) Date of Patent: Jul. 5, 2016

(54) IMAGE PROCESSING METHOD AND APPARATUS

(71) Applicants: KABUSHIKI KAISHA TOSHIBA, Minato-ku (JP); Toshiba Medical Systems Corporation, Otawara-shi (JP)

(72) Inventor: Magnus Wahrenberg, Edinburgh (GB)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/603,905

(22) Filed: Jan. 23, 2015

(51) Int. Cl.
*G06K 9/00* (2006.01)
*G06T 7/00* (2006.01)
*G06T 15/08* (2011.01)

(52) U.S. Cl.
CPC .............. *G06T 7/0012* (2013.01); *G06T 15/08* (2013.01); *G06T 2207/10136* (2013.01)

(58) Field of Classification Search
USPC ........................................................ 382/128
See application file for complete search history.

(56) References Cited

U.S. PATENT DOCUMENTS

| | | | | |
|---|---|---|---|---|
| 5,911,691 | A * | 6/1999 | Mochizuki | G01S 7/52073 128/916 |
| 5,999,187 | A * | 12/1999 | Dehmlow | G06T 19/003 345/420 |
| 6,450,962 | B1 | 9/2002 | Brandl et al. | |
| 2006/0279568 | A1* | 12/2006 | Matsumoto | G06T 19/00 345/419 |
| 2010/0185091 | A1* | 7/2010 | Sumi | A61B 8/08 600/443 |
| 2011/0181590 | A1* | 7/2011 | Brabec | G06T 15/00 345/424 |
| 2011/0184288 | A1 | 7/2011 | Kawabata et al. | |
| 2011/0262023 | A1* | 10/2011 | Brabec | G06T 5/002 382/131 |
| 2012/0127200 | A1* | 5/2012 | Kohara | G06T 15/08 345/629 |
| 2013/0257860 | A1 | 10/2013 | Tezuka et al. | |
| 2013/0258804 | A1 | 10/2013 | Fujii | |
| 2014/0232719 | A1 | 8/2014 | Wahrenberg | |
| 2014/0350403 | A1* | 11/2014 | Kho | A61B 8/483 600/442 |
| 2016/0042530 | A1* | 2/2016 | Imber | G07G 1/0081 382/162 |
| 2016/0042556 | A1* | 2/2016 | Imber | G07G 1/0081 345/426 |

FOREIGN PATENT DOCUMENTS

| | | |
|---|---|---|
| JP | 2003-204963 | 7/2003 |
| JP | 2007-135841 | 6/2007 |
| JP | 2010-184117 | 8/2010 |
| JP | 2013-13650 | 1/2013 |
| JP | 2013-230352 | 11/2013 |
| WO | 2012/090658 A1 | 7/2012 |

OTHER PUBLICATIONS

"The Henyey-Greenstein phase function", http://www.astro.umd.edu/~iph/HG_note.pdf, 1941, 6 pages.

* cited by examiner

*Primary Examiner* — John Strege
(74) *Attorney, Agent, or Firm* — Oblon, McClelland, Maier & Neustadt, L.L.P

(57) ABSTRACT

An image processing apparatus comprising a volume data unit for obtaining a volumetric image data set, and a rendering process unit configured to set a position of a light source, determine a plurality of sample points with respect to the volumetric image data set, for each sample point, determine at least one offset point, wherein the or each offset point is positioned at a respective offset distance from the sample point, for each offset point, determine an irradiance arising from light virtually emitted from the light source, determine or refine an irradiance at each sample point based on the irradiance at its respective at least one offset point, and render, based on the determined or refined irradiances at the sample points, an image.

18 Claims, 9 Drawing Sheets

Single Volume Performance

|  | | Cartesian Volume Size (^3) | | |
|---|---|---|---|---|
|  | | 180 | 216 | 256 |
| Volume Downsize Level | 2 | 8.62 | 8.23 | 7.5 |
|  | 2+L | 7.87 | 7.67 | 7.2 |
|  | 1 | 6.07 | 4.74 | 3.7 |
|  | 0 | 2.13 | 1.45 | 1 |

Fig. 8

IMAGE PROCESSING METHOD AND APPARATUS

FIELD

Embodiments described herein relate generally to a method of, and apparatus for enhancing detail in medical images, for example global illumination images.

BACKGROUND

It is known to use ultrasound to image anatomical structures by transmission and reception of ultrasound waves from a transducer. Ultrasound imaging may often be applied to image the fetus in the womb.

Three-dimensional (3D) ultrasound images may be obtained by using software to combine ultrasound data that has been taken at different positions or angles to obtain volumetric ultrasound data, and to render an image from the volumetric ultrasound data using methods such as simple surface shading or direct volume rendering. The rendered image may be represented as a 2D rendered image data set, which comprises appropriate pixel color values for display on a 2D surface such as a 2D screen. Such rendered images may nonetheless be referred to as 3D images because they provide an image that the viewer perceives as being representative of a structure in three dimensions, for example a solid structure.

In four-dimensional (4D) ultrasound imaging systems, a series of 3D images obtained at different times is dynamically rendered to produce a moving 3D image, for example a 3D ultrasound movie.

In recent years, 3D and 4D ultrasound images have been made more realistic through the use of advanced lighting techniques (referred to, for example, as global illumination, gradient free lighting, subsurface scattering or photon mapping) that simulate illumination with a more physically accurate model than was previously used.

In global illumination, a lighting model may be used that includes both direct illumination by light coming directly from a light source and indirect illumination, for example illumination by light that has been scattered from another surface.

Global illumination in ultrasound has gone from being seen as a novelty to being, in some cases, a required feature of ultrasound systems. In obstetrics, global illumination may be used to provide high quality images of the fetal face. Global illumination may also be of interest to doctors in other specialties, For example, global illumination may be used to render images from abdominal scans, so as to produce images that may in some cases be easier to read and/or contain greater detail than those produced with simpler lighting models. It is expected that the recognition and importance of global illumination may continue to increase.

Volume rendering may be computationally costly. FIG. 1 shows a cubic grid of voxels for which width=height=depth=N. The complexity of the volume rendering for this cube may be of the order of $N^3$ (all the voxels may have to be taken into account).

Volume rendering for which global illumination is used may be even more computationally costly than volume rendering without global illumination. A naïve method for simple lighting configurations may include of the order of $N^4$ operations.

There are global illumination methods that transform the global illumination process into two passes. Using such methods, the complexity of rendering may be considered to be reduced to be on the order of $2*N^3$. One such method is photon mapping. Other methods are also available that perform two passes, which may be referred to as traversals.

A first pass may create a light volume, and a second pass may use the light volume to render an image for display. A two-pass system may allow a single light volume to be used for multiple rendering passes at different viewing angles, thus avoiding the need to recalculate the light volume for each render.

A volumetric image data set comprises an array of voxels, each with an associated intensity. A volumetric image data set may be obtained directly from a medical imaging scan or through further processes such as reconstruction and filtering.

The volumetric image data set may be representative of all or part of the subject of the scan. The intensities of the voxels may correspond to physical properties of the subject of the scan, for example tissue types. The intensities may be mapped on to opacity and color values, for example by using a transfer function.

The volumetric image data set contains a representation of materials, surfaces and so on that occur in the subject. In the discussion below, processes may be referred to as if they occurred in a physical space (for example, light reflecting from a surface). However, in the case of illumination, we are usually describing virtual (simulated) processes occurring as numerical operations on a volumetric image data set. Similarly, when we discuss the volumetric image data set as if it were a physical space having a physical extent, we are generally referring to the coordinate space that is represented by the voxels of the image volume.

In order to render an image from the volumetric image data set, the position of at least one light source may be determined with reference to the volumetric image data set. The position of a viewpoint (which may be referred to as a camera) may also be determined. The image will be rendered as if viewed from the viewpoint.

A first pass may comprise a traversal from the light source into the volumetric image data set, in which virtual light is cast into the volumetric image data set. A global illumination lighting model may be used. The irradiance due to the light source may be determined at each of a large array of points in the volumetric image data set using absorptive properties assigned to the voxels in dependence on the voxel intensities.

The irradiance values at the array of points may be stored as a light volume. The light volume may be stored in memory. The light volume may be independent of the viewpoint.

The irradiance of each voxel in the light volume is determined by the number of photons that passes through the voxel. For better numerical performance, photons are often treated in a statistical way, rather than in a discrete way. This means that light from the light source may act as a beam of light sometimes, but like a discrete photon at other times.

Absorption may be more efficient to describe statistically, usually as an integral formed by the Beer-Lambert law. Absorption as defined by the Beer-Lambert law is governed by a medium-specific coefficient called the attenuation coefficient. The attenuation coefficient has a range of $[0,\infty]$ and may be used synonymously with opacity. Opacity is often defined on a $[0,1]$ range, indicating what fraction of the light is absorbed.

Reflection and scattering and refraction may be seen as events that can happen along the light path and as such may be part of the determination of each voxel's irradiance.

A second pass may comprise a traversal through the light volume from the camera, using the light volume to provide global lighting information. Rays may be cast from the camera (for example, one ray for each pixel of the resulting rendered image), and irradiances from points along each ray may be integrated to provide pixel color values for a final rendered image.

BRIEF DESCRIPTION OF THE DRAWINGS

Embodiments are now described, by way of non-limiting example, and are illustrated in the following figures, in which:

FIG. 8 is a table of results of a range of rendering scenarios with and without irradiance refinement;

DETAILED DESCRIPTION

Certain embodiments provide an image processing apparatus comprising a volume data unit for obtaining a volumetric image data set, and a rendering process unit configured to set position of a light source, and determine a plurality of sample points with respect to the volumetric image data set. The rendering process unit is configured to, for each sample point, determine at least one offset point, wherein the or each offset point is positioned at a respective offset distance from the sample point. The rendering process unit is configured to, for each offset point, determine an irradiance arising from light virtually emitted from the light source. The rendering process unit is further configured to determine or refine an irradiance at each sample point based on the irradiance at its respective at least one offset point and render, based on the determined or refined irradiances at the sample points, an image.

Certain embodiments provide an image processing method comprising: obtaining a volumetric image data set; setting position of a light source; determining a plurality of sample points with respect to the volumetric image data set; for each sample point, determining at least one offset point, wherein the or each offset point is positioned at a respective offset distance from the sample point; for each offset point, determining an irradiance arising from light virtually emitted from the light source; determining or refining an irradiance at each sample point based on the irradiance at its respective at least one offset point; and rendering, based on the determined or refined irradiances at the sample points, an image.

Figure 1:
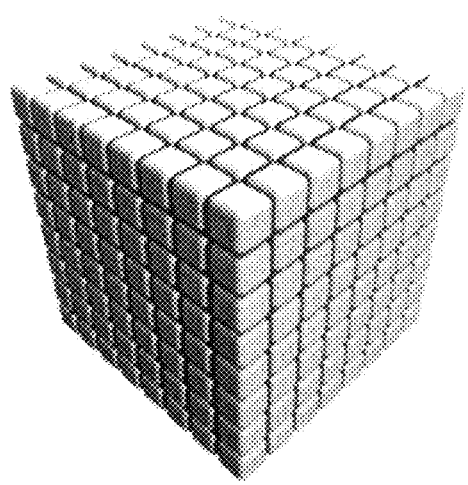
FIG. 1 is a diagram representing a volume of side N.
Figure 2:
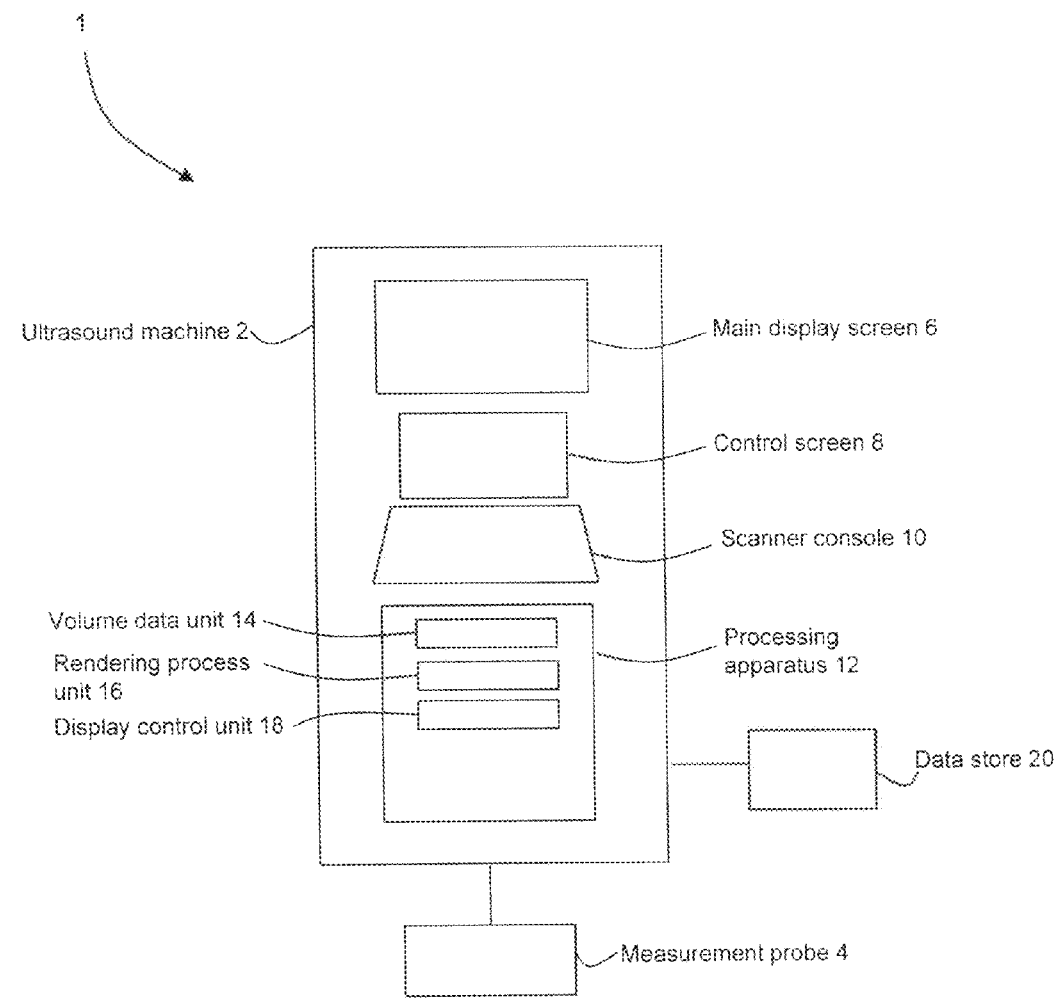
FIG. 2 is a schematic diagram of an image processing apparatus according to an embodiment.

A medical diagnostic apparatus 1 according to an embodiment is illustrated schematically in FIG. 2. In the present embodiment, medical diagnostic apparatus 1 is configured to acquire volumetric image data from a medical imaging scan, to process the acquired volumetric image data and to render an image from the processed volumetric image data. In alternative embodiments, an image processing apparatus is configured to receive volumetric image data that has been acquired by scanner (such as an ultrasound machine, CT scanner, MR scanner, PET scanner or SPECT scanner), to process the received volumetric image data and to render an image from the processed volumetric image data.

In the present embodiment, the medical diagnostic apparatus 1 comprises an ultrasound machine 2 and associated measurement probe 4. Any suitable type of ultrasound machine 2 and measurement probe 4 may be used, for example any ultrasound machine 2 and transducer probe 4 that are configured to obtain ultrasound image data that is suitable for 3D or 4D imaging.

Although in the present embodiment the medical diagnostic apparatus 1 comprises an ultrasound machine 2, in other embodiments the medical diagnostic apparatus 1 may comprise an apparatus of an alternative modality, for example a CT scanner, MR scanner, PET scanner or SPECT scanner.

The ultrasound machine 2 comprises a main display screen 6 for displaying a main ultrasound image, a control screen 8 for displaying control information, and a scanner console 10. In this embodiment, the scanner console 10 comprises an input device or devices such as input buttons or knobs, a computer keyboard, a mouse or a trackball. In alternative embodiments, the control screen 8 is a touch screen, which is both a display device and a user input device. Further embodiments may comprise a control screen 8, display screen or main display screen 6 that does not form part of the ultrasound machine 2. The ultrasound machine 2 also comprises a data store 20 for storing volumetric image data.

The ultrasound machine 2 comprises a processing apparatus 12 for processing of data, including image data. The processing apparatus 12 comprises a Central Processing Unit (CPU) and Graphical Processing Unit (GPU). The processing apparatus 12 includes a volume data unit 14 for generating or receiving volume data and a rendering process unit 16 for rendering an image from the volume data. In the present embodiment, the processing apparatus 12 also comprises a display control unit 18 for display of rendered images. The volume data unit 14, rendering process unit 16 and display control unit 18 may each be implemented in the CPU, in the GPU, or in a combination of the CPU and the GPU.

In alternative embodiments the processing apparatus 12 comprising the volume data unit 14, rendering process unit 16 and display control unit 18 may be part of any suitable medical diagnostic apparatus (for example a CT scanner or MR scanner) or image processing apparatus (for example, a PC or workstation). The processing apparatus 12 may be configured to process any appropriate modality of volumetric image data, for example ultrasound, CT, MR, PET or SPECT data.

In the present embodiment, the volume data unit 14, rendering process unit 16 and display control unit 18 are each implemented in the CPU and/or GPU of processing apparatus 12 by means of a computer program having computer-readable instructions that are executable to perform the method of the embodiment. However, in other embodiments each unit may be implemented in software, hardware or any suitable combination of hardware and software. In some embodiments, the various units may be implemented as one or more ASICs (application specific integrated circuits) or FPGAs (field programmable gate arrays).

The processing apparatus 12 also includes a hard drive and other components including RAM, ROM, a data bus, an operating system including various device drivers, and hardware devices including a graphics card. Such components are not shown in FIG. 2 for clarity.

Figure 3:
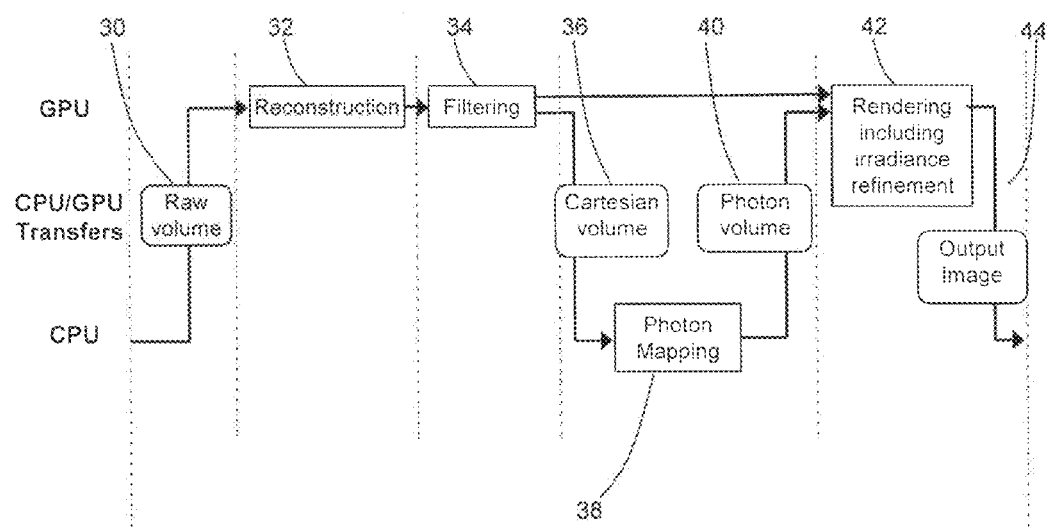
FIG. 3 is a flowchart illustrating in overview the process of an embodiment.

The system of FIG. 2 is configured to perform a process having a series of stages as illustrated in overview in the flow chart of FIG. 3. FIG. 3 is structured so as to illustrate, for the present embodiment, which steps are performed in the CPU and which in the GPU of processing unit 12. In alternative embodiments, some or all of the steps indicated in FIG. 3 as being performed in the CPU may take place in the GPU, and vice versa.

A raw ultrasound volume 30 is acquired by the ultrasound machine 2 using the measurement probe 4. The raw ultrasound volume 30 is passed from the CPU to the GPU.

The raw ultrasound volume 30 is representative of echo signals obtained by ultrasonic transmission and reception to and from a three-dimensional region of a subject. The imaged three-dimensional region contains an observational target, which is the structure to be imaged. For example, in some embodiments, the three-dimensional region is the abdomen and the observational target is the liver or the kidney.

In the present embodiment, the raw ultrasound volume 30 is representative of at least part of a fetus (the fetus is the observational target). In other embodiments, the raw ultrasound volume 30 may represent any structure suitable for imaging by ultrasound. For example, the raw ultrasound volume may represent a gallbladder, liver, kidney, bladder, uterus or other abdominal organ.

In the present embodiment, the raw ultrasound volume 30 comprises data points acquired in the native format of the ultrasound scanner, which comprises a fan geometry. At stage 32, the volume data unit 14 performs a reconstruction on the raw ultrasound volume 30 to obtain Cartesian data (data arranged along straight axes that are orthogonal to each other). Stage 32 results in an initial Cartesian volume that comprises a regular three-dimensional array of voxels.

Any suitable method of reconstruction may be used in stage 32, for example reconstruction comprising any suitable form of interpolation. In embodiments in which an alternative imaging modality is used, the acquired data may already be in a Cartesian form and stage 32 may be omitted.

At stage 34, the volume data unit 14 performs filtering on the initial Cartesian volume to obtain a resulting Cartesian volume 36. The filtering may comprise applying a filter to reduce noise that is present in the initial Cartesian volume. Any suitable filter or combination of filters may be used at stage 34. In some embodiments, particularly those with less noisy imaging modalities, stage 34 may be omitted. The volume data unit 14 passes Cartesian volume 36 from the GPU to the CPU.

In alternative embodiments, the Cartesian volume 36 has been obtained previously (for example, by a scan procedure occurring prior to the image rendering process of FIG. 3). The volume data unit 14 receives a Cartesian volume 36, for example from data store 20. Stages up to and including stage 34 are omitted.

The Cartesian volume 36 comprises an array of voxels. Each voxel has a position in the coordinate space of the Cartesian volume and an associated signal intensity (which may have been interpolated from intensities in the raw ultrasound data, the raw ultrasound data being representative of the ultrasound signal capture). Different tissue types may produce different signal intensities. Each intensity may be associated with an opacity and/or a color. For example, a transfer function may be used to relate intensity to opacity and/or color.

At stage 38 (which may be considered to be the first pass of a two-pass rendering process) the rendering process unit 16 performs a photon mapping on the Cartesian volume 36 to obtain a photon volume 40. (The photon volume 40 may also be described as a light volume or spectral irradiance volume, and shows light energy distribution in the volume.) The photon mapping of stage 38 is described below with reference to the schematic diagram of FIG. 4.

Figure 4:
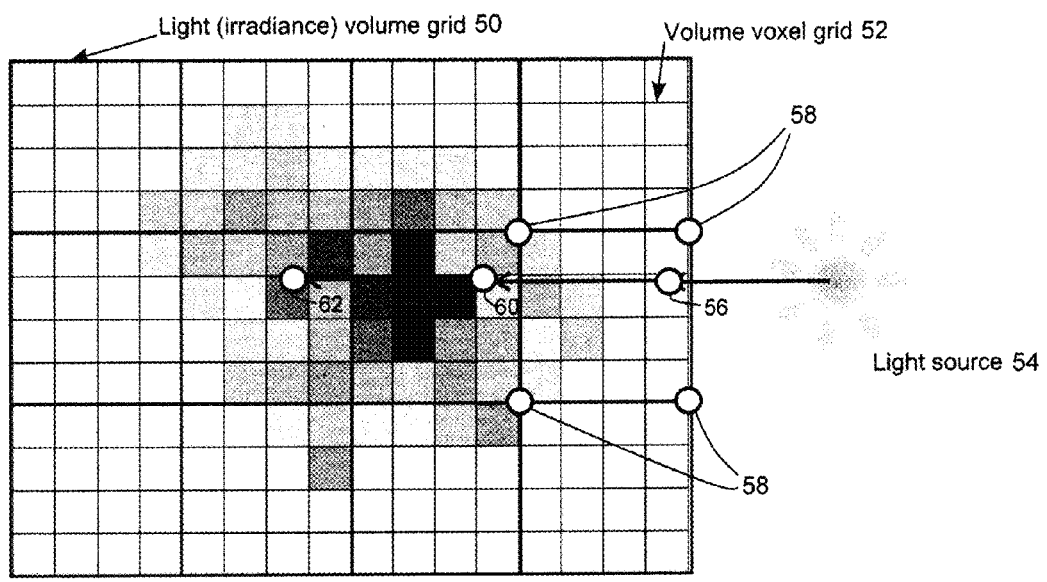
FIG. 4 is a schematic diagram illustrating the progress of a ray from a light source in a first pass.

FIG. 4 is a schematic diagram which is representative of a slice through Cartesian volume 36. The volume voxel grid 52 is representative of the positioning of voxels within the Cartesian volume 36. Each corner (intersection of lines) of the volume voxel grid 52 is representative of the center of a voxel (the voxel center is exactly aligned with the grid under interpolation). The grayscale shading of each box of the volume voxel grid 52 is representative of an absorption associated with voxels in that region.

In the present embodiment, the absorption function for each voxel is a function having color-dependent absorption properties, and may be described as a spectral absorption. The absorption function is defined such that blue and green light are absorbed more strongly than red light, to represent the absorption of tissue. The grayscale shading represents the absorption at one frequency. Absorption functions are associated with voxel intensities by using a transfer function. Absorption functions may be associated with voxels by the rendering process unit 16, or by the volume data unit 14 at an earlier stage of the process of FIG. 3.

Although only a slice of the volume voxel grid 52 is represented in FIG. 4, the volume voxel grid 52 should be considered as a three-dimensional grid that extends throughout the Cartesian volume 36.

The rendering process unit 16 determines a light (irradiance) volume grid 50 comprising an array of reference points at which irradiance is to be calculated. The positions of the reference points may or may not be coincident with the positions of voxels in the volume voxel grid 52.

In the present embodiment, the light volume grid 50 is a downsampled version of volume voxel grid 52. Therefore the reference points of the light volume grid will be referred to as downsampled voxels in the discussion below. It may be understood that in alternative embodiments, the light volume grid may not be downsampled, and may instead have the same voxel size as the volume voxel grid 50.

In FIG. 4, the light volume grid 50 is represented by bold lines and the volume voxel grid 52 is represented by lines of a normal weight. The light volume grid 50 is a downsampling of the volume voxel grid 52 by a factor of 4 per side (therefore, the ratio of the number of downsampled voxels in the light volume to the number of voxels in the image volume is 1:256). In other embodiments, a different downsampling factor may be used, or no downsampling may be performed.

The rendering process unit 16 defines a position of at least one virtual light source relative to the Cartesian volume. In the present embodiment, a single light source 54 is placed outside the boundary of the volumetric image data set. However, in alternative embodiments, two or more light sources may be used. In some cases, a light source position may be inside the volume represented by the volumetric image data set, for example inside the volume represented by the volumetric image data set but outside the observational target (for example, the fetus).

The rendering process unit 16 simulates the casting of light from light source 54 into the Cartesian volume 36. The light may be considered as a set of light rays radiating from the light source 54 into the Cartesian volume 36. Each light ray comprises a large number of photons. Each photon is traced from the light source 54 as it interacts with the Cartesian volume to the point that it is absorbed. The progress of one of the light rays (represented by arrows) is illustrated in FIG. 4.

The ray enters the Cartesian volume 36 from the direction of the light source 54. The rendering process unit 16 calculates the irradiance for each of a set of points on the ray, the points being separated by a fixed increment in length (represented in FIG. 4 as the length of each arrow). In the embodiment of FIG. 4, each light ray steps through the voxel in increments of 4× the voxel spacing (=1× the downsampled voxel spacing). In alternative embodiments, different increments may be used. In some embodiments, increment lengths may vary along the ray.

As the ray traverses the volume from the light source 54, it distributes virtual light energy to the local voxel neighborhood around points that it passes through. As the ray progresses, the amount of light absorbed is computed and when all the light is absorbed the traversal is terminated.

To consider the progress of the ray shown in FIG. 4, the ray is first considered at point 56 (which is not coincident with the position of any voxel in the Cartesian volume). The rendering process unit 16 determines the absorption between the light source 54 and point 56 using the absorption function associated with any voxels between the light source 54 and point 56, and thereby determines the irradiance due to the light at point 56.

In the present embodiment, a gray value from the volume is generated with interpolation. The spatial region of the current position (point 56) is determined to belong to one or many objects. A given voxel belongs to an object if the position of the voxel is classified as a part of the object. Objects may comprise, for example, selections, organs, vessels, or pathology (for example, tumors or aneurysms). The rendering process unit 16 may assign different optical properties to different objects to differentiate them visually.

The spatial object classification may be provided using a binary volume, a mesh, a plane, or similar structures. In some embodiments, binary volumes are used. In the present embodiment, a volume is used in which each voxel represents the object number corresponding to that location. This may have the same effect as multiple binary volumes where objects do not overlap. Each object has a transfer function that maps the interpolated gray value to the spectral attenuation coefficients of the absorption function.

If multiple objects overlap (which is not the case in the implementation of the present embodiment), then multiple independent attenuation coefficients are produced and may be combined by, for example, addition, averaging, or taking a maximum.

For additional smoothness, the attenuation coefficient may be modulated by interpolated volume to force smooth transitions. Clip planes may also apply such modulation, then as a function of the distance to the clip plane. In some embodiments, scattering may also be determined by a per-object transfer function.

In the example illustrated in FIG. 4, no light is absorbed between the light source 54 and point 56 (there being no absorptive material present between the light source and point 56) and therefore the irradiance at point 56 is 100% of the irradiance originating from the light source 54.

The irradiance calculated at each point is a spectral irradiance, which may be described as a combination of red, green and blue components (or, more generally, an irradiance per wavelength for the full spectrum of relevant wavelengths).

At point 56, since there has been no absorption, the light is white. The irradiance may be expressed in $W/m^3$, or as an uncalibrated value. For example, the irradiance may be normalized to the radiant energy emitted from the light source 54.

Although in the present embodiment, the determined irradiance is a spectral irradiance, in other embodiments the determined irradiance may not be a spectral irradiance (the determined irradiance may not have a color component).

In the present embodiment, the calculated irradiance is not directional.

In other embodiments, an associated irradiance direction may be determined at each point for which irradiance is calculated. The irradiance direction may be the direction of incidence of the light received at that point.

In some embodiments, at each point, an irradiance is calculated for each of a plurality of irradiance directions. In some embodiments, at each point, an irradiance distribution is determined across all angles.

The rendering process unit 16 distributes the irradiance at point 56 between the nearest downsampled voxels of the light volume grid 50. In FIG. 4, the four nearest downsampled voxels are indicated as points 58. Although when represented in two dimensions each point in the volume has four nearest neighbor downsampled voxels, in a three-dimensional Cartesian grid each point has eight nearest neighbors. Therefore in the three-dimensional case, the irradiance from point 56 is distributed between eight nearest neighbor downsampled voxels 58.

Any suitable method may be used to distribute irradiance from a point to neighboring voxels. Distributing the irradiance from each point may be considered to be the reverse of interpolation. Therefore particular methods of distribution may be analogous to particular methods of interpolation. Distributing to eight nearest neighbors may be considered to be analogous to trilinear interpolation. Different footprints may be used for the distribution of irradiance. In some embodiments, instead of a footprint of eight nearest neighbors (a 2×2×2 footprint) to which irradiance is distributed, a cubic 4×4×4 footprint is used. In further embodiments, a more complicated footprint is used.

The amount of irradiance distributed to each neighboring downsampled voxel may be dependent on the distance from point 56 to the downsampled voxel. The amount of irradiance allocated to each voxel may be inversely proportional to the distance from point 56 to each of the downsampled voxels. In a case in which the point on the ray is coincident with a downsampled voxel position, all of the irradiance from the ray at that point may be given to that downsampled voxel and none distributed between neighbors.

The rendering process unit 16 determines a spectral irradiance at point 60 using the irradiance that has been determined at point 56 and the absorption values for voxels between point 56 and point 60. In the example of FIG. 4, some voxels between point 56 and point 60 have a non-zero absorption, as represented as a grayscale shading of the relevant voxels. The voxels between point 56 and point 60 may be representative of tissue.

The rendering process unit 16 uses the absorption values of the voxels between points 56 and 60 to calculate how much of the irradiance calculated at point 56 is absorbed between points 56 and 60. The translucent effects of tissue may be simulated. For example, there may be expected to be lots of irradiance at a skin surface, and a little less just under the skin.

The amount of absorption may be different for different colors of light. In particular, it is expected that tissue may absorb blue and green light in preference to red light, and therefore the spectral absorption functions may be set such that light becomes redder as it passes through absorptive material.

The rendering process unit 16 distributes the irradiance at point 60 between the eight nearest neighboring downsampled voxels of the light volume grid (or, in other embodiments with a different footprint, distributes the irradiance to the appropriate footprint of voxels, for example to a 4×4×4 set of voxels around the point).

The rendering process unit 16 determines a spectral irradiance at point 62 using the irradiance determined for point 60 and the absorption values of voxels between points 60 and 62. In FIG. 4, there is a large amount of absorption between points 60 and 62 (represented by dark grayscale values) and little irradiance remains at point 62. The color of the irradiance at point 62 is considerably redder than that at point 60, most or all of the blue and green light having been absorbed.

Once a sufficient portion of the light in a particular ray has been absorbed, no further calculations are performed on that ray. In the present embodiment, if 99% of the light in a ray has been absorbed, no further calculations are performed on that ray. In other embodiments, a different proportion of the light may be considered to be a sufficient portion, for example 90% or 95% of the light. In other embodiments, all the light may be required to be absorbed.

The process of casting light as described above is repeated for all rays cast into the Cartesian volume. In the present embodiment, light source 54 is a directional light. All the rays cast into the Cartesian volume are parallel. In other embodiments, light source 54 may be a point light or other form of light that does not have parallel rays. In further embodiments, stochastic light sources may be used, for which the direction is a stochastic variable with a specific distribution.

In the present embodiment, the ray casting process of stage 38 simulates scattering as well as direct illumination. Some photons may be scattered rather than absorbed. In some embodiments, only single scattering is taken into account. In some embodiments, multiple scattering is taken into account.

In some embodiments, reflection is also taken into account. In some embodiments, scattering and/or reflection may be ignored entirely (for example, for complexity or performance reasons). Scattering and/or reflection may be enabled in the first pass (which may not change the data stored in the light volume). Reflection does not apply to the second pass since the second pass represents the last scattering operation in which the light is directed towards the camera.

If multiple scattering is used for the first pass it may be desirable to match the multiple scattering of the first pass with a more accurate scattering model in the second pass. In some embodiments, the more accurate scattering model in the second pass uses a directional irradiance distribution.

In the present embodiment, for each light ray, irradiance is determined at points placed along the ray at intervals that correspond to the downsampled voxel spacing (4× the voxel spacing of the volume voxel grid 52). In other embodiments, irradiance may be determined at different intervals. For example, irradiance may be determined at intervals corresponding to the voxel size of the volume voxel grid 52.

Each downsampled voxel in the light volume grid may receive irradiance contributions from more than one ray, for example from points on rays above, below and to each side of the voxel.

The result of the light casting (photon mapping) process of stage 38 is a photon volume (or light volume) 40 in which each of the downsampled voxels on the light volume grid 50 is associated with a spectral irradiance.

Although the photon mapping process is described only for one light source above, the photon mapping process may be performed for multiple light sources. The ray casting process above may be repeated for each of the multiple light sources. An irradiance may be calculated for each downsampled voxel that comprises contributions from the multiple light sources.

The photon volume 40 is independent of the viewpoint and depends only on the light source position or positions and the voxel properties. Therefore the computation of the photon volume 40 is capable of being used for multiple renderings from different viewpoints. It is possible to query the irradiance at any point in the photon volume 40.

The photon volume 40 is stored in the data store 20. In the present embodiment, the fact that the photon volume 40 has lower spatial resolution than the Cartesian volume 36 (downsampled by a factor of 4 in each dimension) means that the memory required to store the photon volume 40 is considerably less than would be required by a photon volume that was calculated at full resolution (the resolution of the volume voxel grid 52).

The photon volume 40 is passed from the CPU to the GPU. In the present embodiment, the rendering process unit 16 can run processes in either the CPU or the GPU.

At stage 42 (which may be described as the second pass in a two-pass rendering process) the rendering process unit 16 renders a two-dimensional image data set representative of an output image 44 using the pre-computed photon volume 40 and the Cartesian volume 36. As part of the rendering pass, the rendering process unit 16 performs a local irradiance refinement (a further calculation of irradiance at a local level). The irradiance refinement may achieve more accurate irradiance estimation than may be obtained through the photon mapping process of stage 38 alone.

Figure 5:
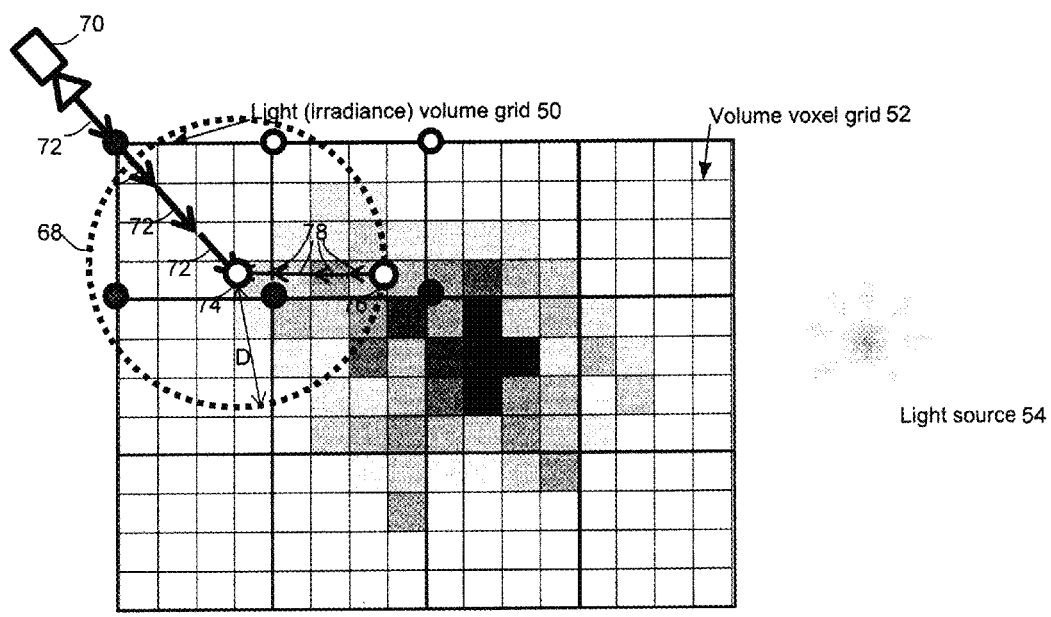
FIG. 5 is a schematic diagram illustrating the progress of a ray from a camera in a second pass.

The rendering process of stage 42 may be described with reference to the schematic diagram of FIG. 5.

The position of a camera 70 and a gaze direction (indicated in FIG. 5 by the direction of arrows 72) are defined by the rendering process unit 16. The camera position may be described as a viewing position. A two-dimensional viewing plane may be defined based on the camera position and the gaze direction (which may also be called a viewing direction).

The rendering process unit 16 casts rays into the volume represented by the volumetric image data set from the direction of the camera. One such ray is shown by arrows 72 of FIG. 5. Each ray may correspond to a pixel of the two-dimensional image data set that is to be obtained by the rendering of stage 42.

In the present embodiment, each ray steps through the volume represented by the volumetric image data set in increments of the volume voxel spacing (represented by arrows 72). In other embodiments, a different increment may be used. Each incremental point along the ray may be called a sample point. If the sample point is representative of empty space the ray skips on to the next sample point.

If the ray reaches a sample point at which material is present, the rendering process unit 16 determines an initial irradiance for the sample point, refines the initial irradiance, and uses the refined irradiance to estimate the light scattering back to the camera. The steps of determining the initial irradiance, refining the initial irradiance and using the refined irradiance to estimate the light scattering are described in more detail below.

When the ray reaches a sample point at which material is present, the rendering process unit 16 determines an initial irradiance at the sample point by interpolating the irradiance from the neighboring downsampled voxels of the light volume. In the example of FIG. 5, the ray reaches sample point 74. The presence of material at sample point 74 is indicated on FIG. 5 by grayscale shading.

If a sample point falls between voxels, the initial irradiance is determined by interpolating irradiance from the eight neighboring downsampled voxels in the volume. If the sample point should coincide with a downsampled voxel, the sample point may be assigned the irradiance of that downsampled voxel as its initial irradiance and no interpolation may be required.

Although in the present embodiment only nearest-neighbor downsampled voxels are considered in the calculation of the initial irradiance, in other embodiments, a greater number of voxels may be considered.

The rendering process unit 16 defines a sphere 68 of a fixed radius D, which is dependent on voxel size. The rendering process unit 16 then defines an offset point spaced away from the sample point by distance D in the direction of the light source. In FIG. 5, offset point 76 is offset from sample point 74 by distance D.

In the present embodiment, distance D is a constant distance, which is used throughout the rendering processing to determine offset point positions. In other embodiments, different distances may be used for different offset points. In the present embodiment, D is the downsampled voxel spacing of the light volume grid (four times the voxel spacing of the volume voxel grid).

The radius D may be considered to be a measure of uncertainty in the photon mapping calculation of stage 38. The uncertainty may depend on a large number of factors, for example, grid size, light source, surfaces within the volume, materials within the volume, or the amount of filtering. However, the uncertainty may be measured by looking at the extent of the irradiance response of an object of that size. In this embodiment, a radius D of 4 is used because it may be seen that features of that size and less may be poorly represented in the irradiance map (photon volume 40). A radius D of 4 may also represent a reasonable level of additional computational complexity for the calculations. In other embodiments, a different value of D may be chosen. For example, a value of D may be chosen in dependence on which feature size is seen to be poorly represented in the photon volume 40 and/or the level of computational complexity that is acceptable in the calculation.

The rendering process unit 16 determines the irradiance at the offset point 76 by interpolating the irradiance values from the offset point's nearest-neighbor downsampled voxels. If the offset point 76 happens to coincide with a light voxel, that light voxel's irradiance is used and no interpolation is performed.

The rendering process unit 16 then simulates the absorption back to the sample point 74, thereby determining a further irradiance value at that sample point 74. In the present embodiment, the rendering process unit 16 steps back from the offset point 76 to the sample point in intervals of one voxel spacing of the volume voxel grid (indicated in FIG. 5 by arrows 78). For each interval, the rendering process unit 16 calculates an irradiance at the end point of the interval from the irradiance at the start point of the interval and the absorption associated with voxels in the local neighborhood. The rendering process unit 16 determines the irradiance at the end of each interval indicated by an arrow 78, resulting in a further irradiance value for the sample point 74 that is determined from the absorptions over the intervals indicated by arrows 78. In alternative embodiments, an irradiance may not be determined for every interval. Instead, the absorptions from all the intervals may be combined to obtain the further irradiance value at the sample point 74.

The number of intervals calculated (in this embodiment, 4), is a constant that is very much less than N=width=depth=height.

In the present embodiment, the absorption calculation within the rendering process 42 is performed at a higher resolution than the absorption calculation of the photon mapping process 38. In the present embodiment, the absorption calculation within the rendering process 42 is performed at a higher resolution than the resolution of the stored photon volume 40. In other embodiments, different resolution may be used. In other embodiments, a different interval may be used to step back from the offset point 76 to the sample point 74 for the calculation of absorption.

In some embodiments, the absorption calculation within the rendering process 42 may be performed even if the photon volume 40 is calculated at full resolution. Such refinement may still provide an improvement to the resulting image, since the tracing of the ray (as, for example, represented by arrows 72) takes place on a continuous grid and the refinement effectively has an element of sub-voxel resolution. Under interpolation even a full-resolution voxel has an extent of at least 2 (−1 to 1) and is affected by additional filtering.

In the present embodiment, the rendering process unit 16 computes a refined irradiance at the sample point by combining 20% of the initial irradiance value with 80% of the further irradiance value.

In other embodiments, different proportions of the initial irradiance value and the further irradiance value may be used to compute a refined irradiance value. For example the refined irradiance may comprise 50% of the further irradiance value plus 50% of the second irradiance value. The refined irradiance may comprise 10% of the initial irradiance value plus 80% of the further irradiance value.

In some embodiments, the refined irradiance value is taken to be the further irradiance value (i.e. the refined irradiance comprises 100% of the further irradiance value and 0% of the initial irradiance value).

In some embodiments, no initial irradiance is calculated at the sample point 74. The irradiance at the offset point is calculated by interpolating the offset point's nearest-neighbor irradiance values and an irradiance value is determined at the sample point 74 using the absorption between the offset point 76 and the sample point 74 as described above with reference to the further irradiance value. References to the refined irradiance below may be replaced by the irradiance that is calculated by stepping back from the offset point 76 (calculated in the same way as the further irradiance value above).

The refined irradiance is used to calculate light scattering back to the camera position from the sample point.

Settings are used that make the light behave in a truly diffuse way. The light is equally likely to be scattered in each direction. If it were possible to factor out reflection, these settings would represent an integral of the irradiance multiplied by a constant (for directional light at least). However, since reflection is not separated, a fixed portion of the light as reflected is applied.

When scattering takes place inside a heterogeneous material or on the surface but coming from inside the heterogeneous material, the light behavior may be modeled using the Henyey-Greenstein phase function. In the present embodiment, settings are applied that turn the Henyey-Greenstein phase function into a constant. In other embodiments, the Henyey-Greenstein phase function may be used more extensively. Since the Henyey-Greenstein phase function does not take into account reflection, reflection may be modeled separately, for example using a polynomial approximation (for example, a Bidirectional Reflectance Distribution Function).

The rendering process unit 16 then moves on to the next sample point on the ray and determines an initial irradiance at that sample point. The rendering process unit 16 determines the position of an offset point relative to that sample point and calculates a further irradiance for the sample point by determining an irradiance at the offset point and stepping back to the sample point using the absorption between the offset point and the sample point. The rendering process unit 16 combines the initial irradiance value and further irradiance value for the sample point to obtain a refined irradiance value. The refined irradiance is used to calculate light scattering back to the camera position from the sample point.

The rendering process unit 16 repeats the process of determining a refined irradiance value for every point on the ray, and integrates the resulting light scattered from each sample point to obtain a pixel color value for that ray.

The rendering process unit 16 repeats the above process for each of a plurality of rays, each corresponding to a respective pixel in a two-dimensional image data set corresponding to an image for display (output image 44). The rendering process unit 16 thereby determines a color value for each pixel in the two-dimensional image data set.

The two-dimensional image data set that is representative of the output image 44 is passed from the GPU to the CPU. The display control unit 18 causes display of the output image 44 on the main display screen 6.

By performing a local irradiance refinement as part of the rendering pass at stage 42, in some circumstances more detail may be present in output image 44 than would be achieved if the image were rendered using the photon volume 40 without irradiance refinement.

Although the irradiance refinement due to only one light source is described above, in other embodiments irradiance may be refined based on multiple light sources. Multiple offset points may be determined for each sample point, one in the direction of each light source.

The determining of refined irradiance values from offset points in the direction of a given light source may be referred to as a refinement traversal. In some embodiments, a separate refinement traversal is performed for each light source. For a sample point, in each traversal, an offset point is determined in the direction of the respective light source and the absorption between the offset point and the sample point is used to determine an irradiance at the sample point. The determined irradiance may be used to refine an initial irradiance at that sample point. A refined irradiance may be calculated by combining an initial irradiance and irradiances from different offset points.

In some embodiments, all offset points are at the same distance D from the sample point, in the direction of the various light sources. In other embodiments, different distances D may be used for different offset points.

In other embodiments, a single irradiance refinement traversal may be performed even where multiple light sources are present, by determining an approximation to the multiple light sources.

In an embodiment in which two light sources are present, the photon volume 40 contains information about both light sources. One of the light sources is selected for refinement within the rendering step 42, and the weighting of the refinement is decreased to adapt the refinement to the scene. Therefore in this embodiment only one refinement traversal is performed despite two light sources being present.

Instead of separating the photon mapping step and the rendering step as in previously-known methods, the method of FIG. 3 allows a constant amount of a photon mapping process to happen during the rendering step, thereby refining the irradiance estimate resulting from the photon mapping step (stage 38). Since the refinement of irradiance is local, it may be computationally relatively inexpensive.

To compare the results of rendering using local irradiance refinement at stage 42 versus rendering without local irradiance refinement at stage 42, an image was rendered using both methods. The image was also rendered using different levels of downsampling (without local irradiance refinement)

Figure 6:
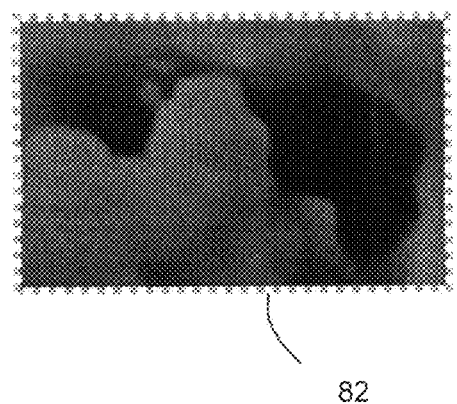
FIG. 6 shows part of a rendered image.
Figure 7:
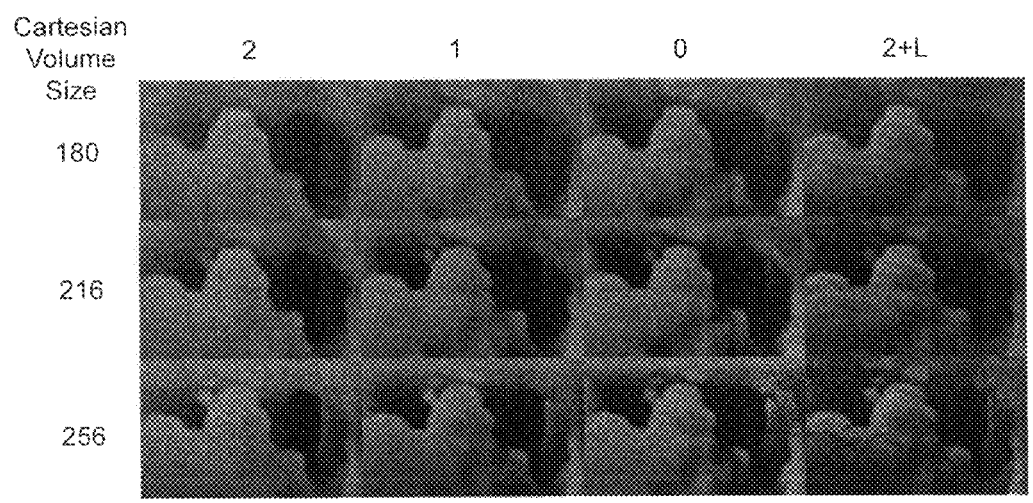
FIG. 7 shows part of a rendered image for a range of rendering scenarios with and without irradiance refinement.

. A small part 82 of the image, shown in FIG. 6, is selected for comparison between the different rendering conditions. This small part 82 is shown in FIG. 7 for multiple rendering scenarios, the details of which are described below.

A volumetric image data set was rendered using four different rendering scenarios:

a) The photon volume 40 was calculated and stored using a downsampled light volume grid that was downsampled by a factor of 4 per side as compared to the volume voxel grid of the Cartesian volume. No irradiance refinement was performed, (This scenario is represented in the column indicated by 2 in FIG. 7.)

b) The photon volume 40 was calculated and stored using a downsampled light volume grid that was downsampled by a factor of 2 per side as compared to the volume voxel grid of the Cartesian volume. No irradiance refinement was performed. (This scenario is represented in the column indicated by 1 in FIG. 7.)

c) The photon volume 40 was calculated and stored using light volume grid that was not downsampled as compared to the volume voxel grid of the Cartesian volume. No irradiance refinement was performed. (This scenario is represented in the column indicated by 0 in FIG. 7.)

d) The photon volume 40 was calculated and stored using a downsampled light volume grid that was downsampled by a factor of 4 per side as compared to the volume voxel grid of the Cartesian volume. Irradiance refinement was performed as described above with reference to the flow chart of FIG. 3. (This scenario is represented in the column indicated by 2+L in FIG. 7.)

For each scenario, the rendering process was performed for each of three Cartesian volume sizes: 180 voxels per side, 216 voxels per side, and 256 voxels per side.

It may be seen from the images presented in FIG. 7 that, when no irradiance refinement is performed, more detail is present in the images for which the photon volume was not downsampled than is present in the images with the downsampled photon volume. For example, the images in column 0 (not downsampled) have considerably more detail than the images of column 2 (downsampled by a factor of 4 per side).

However, from the images of FIG. 7, it may be seen that the images of column 2+L have a high level of detail, which may be comparable to or exceed the level of detail observed in the images of column 0. Therefore, using a photon volume that is downsampled by a factor of 4 per side and performing local irradiance refinement may produce an image that has comparable or better detail to using a photon volume that is not downsampled and is stored at full resolution.

By using a downsampled photon volume, memory requirements may be reduced compared to using a photon volume that is not downsampled. It may also be the case that images may be rendered faster when using a downsampled photon volume than when using a photon volume at full resolution.

FIG. 8 is a table that compares the performance of the four scenarios described above in terms of how quickly images may be rendered using each scenario. Once again the scenarios are labeled as 2 (photon volume downsampled by 4, no irradiance refinement), 1 (photon volume downsampled by 2, no irradiance refinement), 0 (photon volume at full resolution, no irradiance refinement) and 2+L (photon volume downsampled by 4 with irradiance refinement). All scenarios were run on the same hardware using the same volumetric image data set.

A normalized rendering speed for each scenario is given for Cartesian volume sizes of 180, 216 and 256 per side. Speeds are normalized to the slowest rendering speed (a volume size of 256 per side at full resolution), which may be measured in frames per second. The results in the table of FIG. 8 correspond to the images of FIG. 7.

As may be expected, where there is no irradiance refinement, a scenario with a downsampled photon volume results in a faster rendering speed than one in which the photon volume is stored at full resolution. (For example, a Cartesian volume of size 180 runs at a normalized speed of 8.62 when a downsampling factor of 4 is used, for a downsampling factor of 2, and 2.13 for no downsampling.)

The results of FIG. 8 indicated that using irradiance refinement only produces a relatively small reduction in the number of frames per second when compared with the same level of downsampling of the photon volume and no irradiance refinement.

For example a Cartesian volume of size 180 runs at a normalized speed of 8.62 when a downsampling factor of 4 is used without irradiance refinement, and 7.87 with irradiance refinement. In the results of FIG. 8, the difference is less for larger Cartesian volumes. A Cartesian volume of size 256 runs at a normalized speed of 7.5 when a downsampling factor of 4 is used without irradiance refinement, and at 7.2 with irradiance refinement In a clinical setting, there may be a need for a particular rate of frames per second to ensure that the image can be updated fast enough for the clinician's use. For example, in an ultrasound scan in which a sonographer is moving a probe over a patient, it may be required that the displayed image updates at an adequate rate so that the image is representative of the current probe position.

By using a downsampled photon volume with irradiance refinement, it may be possible to achieve a rate of frames per second that is considerably higher than the rate of frames that can be achieved without downsampling, while achieving a detail level in the image that is at least comparable to the detail level of an image using a full resolution photon volume (without irradiance refinement).

The method of FIG. 3 may, in some circumstances, provide detail levels beyond the capability of a previously known two-pass system at the expense of only a small reduction in performance.

Figure 9A:
FIG. 9a is a fetal face image rendered with irradiance refinement.
Figure 9B:
FIG. 9b is a fetal face image rendered without irradiance refinement.

FIG. 9a shows a fetal face image rendered with irradiance refinement. FIG. 9b is a fetal face image rendered without irradiance refinement (for the same level of downsampling). An image rendered using irradiance refinement may have an enhanced level of detail over an image rendered without irradiance refinement.

In one mode of operation, and for one set of example data, the acquisition of volume data took around 23 ms, the reconstruction 32 took around 14 ms, the filtering 34 took either 80 ms (for 8 iterations), 60 ms (for 5 iterations), or 35 ms (for 3 iterations), the stages 36, 38, 40 together took around 33 ms, and the rendering stage 42 and output of a single frame of the image 44 took around 26 ms, giving a total time of 186 to 230 ms corresponding to a frame rate of around 4.3 to 5.4 frames per second.

The use of a downsampled photon volume and irradiance refinement may in some circumstances be faster than other rendering approaches that may give an improvement in detail, for example a shadow ray approach of higher resolution light volume generation.

In some circumstances, the method of FIG. 3 may be applied without increasing, or without significantly increasing, memory consumption above that required by existing two-pass methods (which may use the same size of downsampled photon volume). In In some circumstances, the method of FIG. 3 may increase detail level in output images without significantly increasing memory consumption. In some legacy systems, there may be constraints on memory such that it may not be possible to implement methods requiring increased memory consumption. In some circumstances, it may not be possible to increase the resolution of the photon volume in order to provide an increase in detail.

In previous methods that do not include local irradiance refinement, a doubling of detail level may result in performance dropping by a factor of 4 for the part of the pipeline that does the photon mapping (each ray is traced through the full resolution volume at a full resolution sampling rate whether detail is doubled or not. Therefore the performance drops by a factor of 4 rather than by a factor of 8). By contrast, the method of FIG. 3 may in some circumstances achieve an improvement in detail without such a drop in performance. In some circumstances, the method of FIG. 3 may increase detail level in output images with only a limited reduction in speed. The reduction in speed may be a reduction in speed that is acceptable to a user.

The two passes of the method of FIG. 3 may each have different performance and quality characteristics. For the first pass, local detail may be very computationally expensive. For the second pass, global detail may be very computationally expensive.

Although in the above embodiments the photon volume is calculated and stored at a lower resolution than the volumetric image data set, in other embodiments the photon volume may be calculated and/or stored at the same resolution as the volumetric image data set, or at higher resolution than the volumetric image data set. In some embodiments, some regions of the light volume may be calculated and/or stored at a higher resolution than other regions of the light volume.

In the method of FIG. 3, a global calculation of irradiance at photon mapping stage 38 is refined by a local calculation of irradiance as part of rendering stage 42. References to irradiance above may be replaced by references to illuminance where visible frequencies of light are considered.

Certain embodiments provide a method for increasing the detail level of global illumination comprising a first pass to create a light/irradiance or similar volume, and a second pass to render an image using the light/irradiance volume to support the lighting estimation along a ray, wherein a step is present in the second pass (the rendering pass) to refine the lighting estimation by using the irradiance at a point offset from the ray towards the light source and computing the local absorption between that point and the ray.

The first pass may create a light volume using photon mapping. The first pass may create a light volume using light space volume traversal. The rendering may take multiple lights into account by either approximation or by separating the contribution for each light and doing a refinement traversal for each light.

In some embodiments, multiple refinement traversals may be performed forming a grid of angles and then irradiance may be interpolated between those angles. At least 25 to 64 traversals may be required in such embodiments. Such a grid of angles may apply as an approximation for ambient lights, area lights, or if an extreme number of lights is used.

Ambient, stochastic or area light may be taken into account by approximating or separating the contribution for each type of light and doing a volumetric local refinement traversal for each step.

Although the above embodiments are described in the context of rendering ultrasound images, the method of FIG. 3 may be used to render any appropriate volumetric medical image data, for example CT, MR, PET or SPECT.

Although particular operations are described as being performed in the CPU or in the CPU, in other embodiments any computational distribution between the CPU and the GPU may be used. Any process can happen on either side (CPU or GPU). In some embodiments, the photon mapping may be performed on the GPU.

The embodiments above are described with reference to a global illumination process. In other embodiments, the irradiance refinement described above may be applied to any suitable rendering method, for example a rendering method using at least one of global illumination, photon mapping, light space volume traversal, deep shadow maps, half angle slicing, light propagation volumes or shadow propagation volumes.

Whilst particular units have been described herein, in alternative embodiments functionality of one or more of these units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image processing apparatus comprising:
 a volume data unit for obtaining a volumetric image data set; and
 a rendering process unit configured to:
  set a position of a light source;
  determine a plurality of sample points with respect to the volumetric image data set;
  for each sample point, determine at least one offset point, wherein the at least one offset point is positioned at a respective offset distance from the sample point;
  for each offset point, determine an irradiance arising from light virtually emitted from the light source;
  determine or refine an irradiance at each sample point based on the irradiance at its respective at least one offset point; and
  render, based on the determined or refined irradiances at the sample points, an image.

2. An image processing apparatus according to claim 1, wherein the rendering process unit is further configured to determine for each sample point an initial irradiance arising from light virtually emitted from the light source, and wherein determining or refining the irradiance at each sample point comprises refining the initial irradiance at each sample point.

3. An image processing apparatus according to claim 1, wherein determining or refining the irradiance at a sample point in dependence on the irradiance at an offset point comprises determining absorption between the offset point and the sample point, and determining or refining the irradiance at the sample point based on the irradiance at the sample point and the determined absorption.

4. An image processing apparatus according to claim 1, wherein for each sample point the respective at least one offset point is offset from the sample point substantially in the direction of the light source.

5. An image processing apparatus according to claim 1, wherein the rendering process is configured to perform a light volume process comprising determining a respective irradiance for each of an array of reference points within the volumetric image data set, wherein the irradiances for the array of reference points are determined in dependence on the virtual emission of light from the light source.

6. An image processing apparatus according to claim 5, wherein determining or refining the respective irradiance for each of the sample points comprises, for each sample point, determining an initial irradiance by interpolating irradiances from reference points that are adjacent to the sample point and refining the initial irradiance.

7. An image processing apparatus according to claim 5, wherein determining the respective irradiance for each of the offset points comprises, for each offset point, interpolating irradiances from reference points that are adjacent to the offset point.

8. An image processing apparatus according to claim 5, wherein the volumetric image data set comprises an array of voxels and the array of reference points has lower spatial resolution than the array of voxels.

9. An image processing apparatus according to claim 5, wherein the rendering process unit is configured to perform a first pass calculation and a second pass calculation, wherein the first pass calculation comprises the light volume process and the second pass calculation comprises the determining or refining of the irradiance at each sample point and the rendering of the image.

10. An image processing apparatus according to claim 1, wherein the volume data unit is configured to generate the volumetric image data set by processing echo signals obtained by ultrasonic transmission and reception.

11. An image processing apparatus according to claim 1, wherein the rendering process unit is configured to cast multiple rays, and wherein at least one of the sample points is located along each of the rays.

12. An image processing apparatus according to claim 1, wherein the rendering process unit is configured to set the respective positions of a plurality of light sources and, for each sample point, to determine an irradiance at each of a plurality of offset points, each offset point being positioned at the offset distance from the sample position in the direction of a respective light source; and wherein the rendering process unit is configured, for each sample point, to determine or refine the irradiance at the sample point based on the determined irradiances at the plurality of offset points.

13. An image processing apparatus according to claim 1, wherein the rendering process unit is configured to render the image using at least one of: global illumination, photon mapping, light space volume traversal, deep shadow maps, half angle slicing, light propagation volumes, shadow propagation volumes.

14. An image processing apparatus according to claim 1, wherein the volumetric image data set comprises image data representative of at least part of at least one of a fetus, a gallbladder, a liver, a kidney, a bladder, a uterus, an abdominal organ.

15. An image processing apparatus according to claim 1, wherein the rendering process unit is further configured to set a viewpoint position and gaze direction, and the rendering of the image is performed in dependence on the determined or refined irradiances, the viewpoint position and the gaze direction.

16. A medical diagnostic apparatus comprising:
a scanner for acquiring three-dimensional image data;
a volume data unit for generating from the three-dimensional image data a volumetric image data set;
a data store for storing volumetric image data;
a display screen for displaying medical images;
a rendering process unit configured to:
set a light source position;
determine a plurality of sample points with respect to the volumetric image data set;
for each sample point, determine at least one offset point, wherein the at least one offset point is positioned at a respective offset distance from the sample point;
for each offset point, determine an irradiance arising from light virtually emitted from the light source;
determine or refine an irradiance at each sample point based on the irradiance at its respective at least one offset point; and
render, based on the determined or refined irradiances at the sample points, an image; and
a display control unit, wherein the display control unit is configured to display the rendered image on the display screen.

17. An image processing method comprising:
obtaining a volumetric image data set;
setting a position of a light source;
determining a plurality of sample points with respect to the volumetric image data set;
for each sample point, determining at least one offset point, wherein the at least one offset point is positioned at a respective offset distance from the sample point;
for each offset point, determining an irradiance arising from light virtually emitted from the light source;
determining or refining an irradiance at each sample point based on the irradiance at its respective at least one offset point; and
rendering, based on the determined or refined irradiances at the sample points, an image.

18. A non-transitory computer-readable storage medium storing a computer program comprising computer-readable instructions that are executable to perform a method comprising:
obtaining a volumetric image data set relating to a three-dimensional region of a subject;
setting a position of a light source;
determining a plurality of sample points with respect to the volumetric image data set;
for each sample point, determining at least one offset point, wherein the at least one offset point is positioned at a respective offset distance from the sample point;
for each offset point, determining an irradiance arising from light virtually emitted from the light source;
determining or refining an irradiance at each sample point based on the irradiance at its respective at least one offset point; and
rendering, based on the determined or refined irradiances at the sample points, an image.

* * * * *